（12) United States Patent
Mizota et al.

(10) Patent No.: US 10,429,357 B2
(45) Date of Patent: Oct. 1, 2019

(54) MODEL CREATION METHOD AND DEVICE, AND INSPECTION DEVICE USING THE SAME

(71) Applicant: HITACHI, LTD., Tokyo (JP)

(72) Inventors: Hirohisa Mizota, Tokyo (JP); Yoshiaki Nagashima, Tokyo (JP); Kazuyuki Nakahata, Matsuyama (JP)

(73) Assignee: Hitachi, Ltd., Tokyo (JP)

( * ) Notice: Subject to any disclaimer, the term of this patent is extended or adjusted under 35 U.S.C. 154(b) by 598 days.

(21) Appl. No.: 15/103,929

(22) PCT Filed: Dec. 16, 2013

(86) PCT No.: PCT/JP2013/083545
§ 371 (c)(1),
(2) Date: Jun. 13, 2016

(87) PCT Pub. No.: WO2015/092841
PCT Pub. Date: Jun. 25, 2015

(65) Prior Publication Data
US 2016/0320352 A1 Nov. 3, 2016

(51) Int. Cl.
*G06F 17/50* (2006.01)
*G01N 29/44* (2006.01)
*G01N 23/203* (2006.01)

(52) U.S. Cl.
CPC ....... *G01N 29/4472* (2013.01); *G01N 23/203* (2013.01); *G06F 17/5018* (2013.01); *G01N 2223/602* (2013.01); *G06F 2217/16* (2013.01)

(58) Field of Classification Search
CPC .................................................. G06F 17/5018

USPC ............................................................ 703/2
See application file for complete search history.

(56) References Cited

U.S. PATENT DOCUMENTS

2015/0252224 A1* 9/2015 Iseda .................. C08K 3/08
428/323

FOREIGN PATENT DOCUMENTS

JP 2012-112658 A 6/2012

OTHER PUBLICATIONS

Michio Kadota, Surface Acoustic Wave Properties on Rotated Y-Cut Langasite Single Crystal Substrates, 1998, Murata Manufacturing Co., Ltd, pp. 357-360. (Year: 1998).*
Zhang Guowei, 3D Anisotropy Simulation of Dendrites Growth with Phase-Field Method, 2010, International Conference on Computer Application and System Modeling, pp. 637-640. (Year: 2010).*
(Continued)

*Primary Examiner* — Andy Ho
(74) *Attorney, Agent, or Firm* — Mattingly & Malur, PC

(57) ABSTRACT

There is provided an analysis model creation method which is capable of simply and quickly creating an accurate analysis model with respect to a structure including a crystalline material. In order to solve a problem described above, there is provided a model creation method of an analysis region used in numeral analysis, the method including a step of designating a crystal growth direction if a region is a region including crystallinity including acoustic anisotropy in the analysis region, a step of selecting partial image data to which the crystallinity of the region is reflected, a step of rotating and operating the partial image data along the crystal growth direction, and a step of creating image data which is covered in the region designated using the rotated partial image data.

10 Claims, 13 Drawing Sheets

(56) References Cited

OTHER PUBLICATIONS

J.A. Ogilvy, "Computerized ultrasonic ray tracing in austenitic steel", NDT International, Apr. 1985, vol. 18, No. 2.
Toshiyuki Koyama, "Simulation of Microstructural Evolution Based on the Phase-Field Method and Its Applications to Material Development", The Japan Institute of Metals, 2009, pp. 891-905, vol. 73, No. 12.
International Search Report of PCT/JP2013/083545 dated Mar. 18, 2014.

* cited by examiner

[Fig. 1]
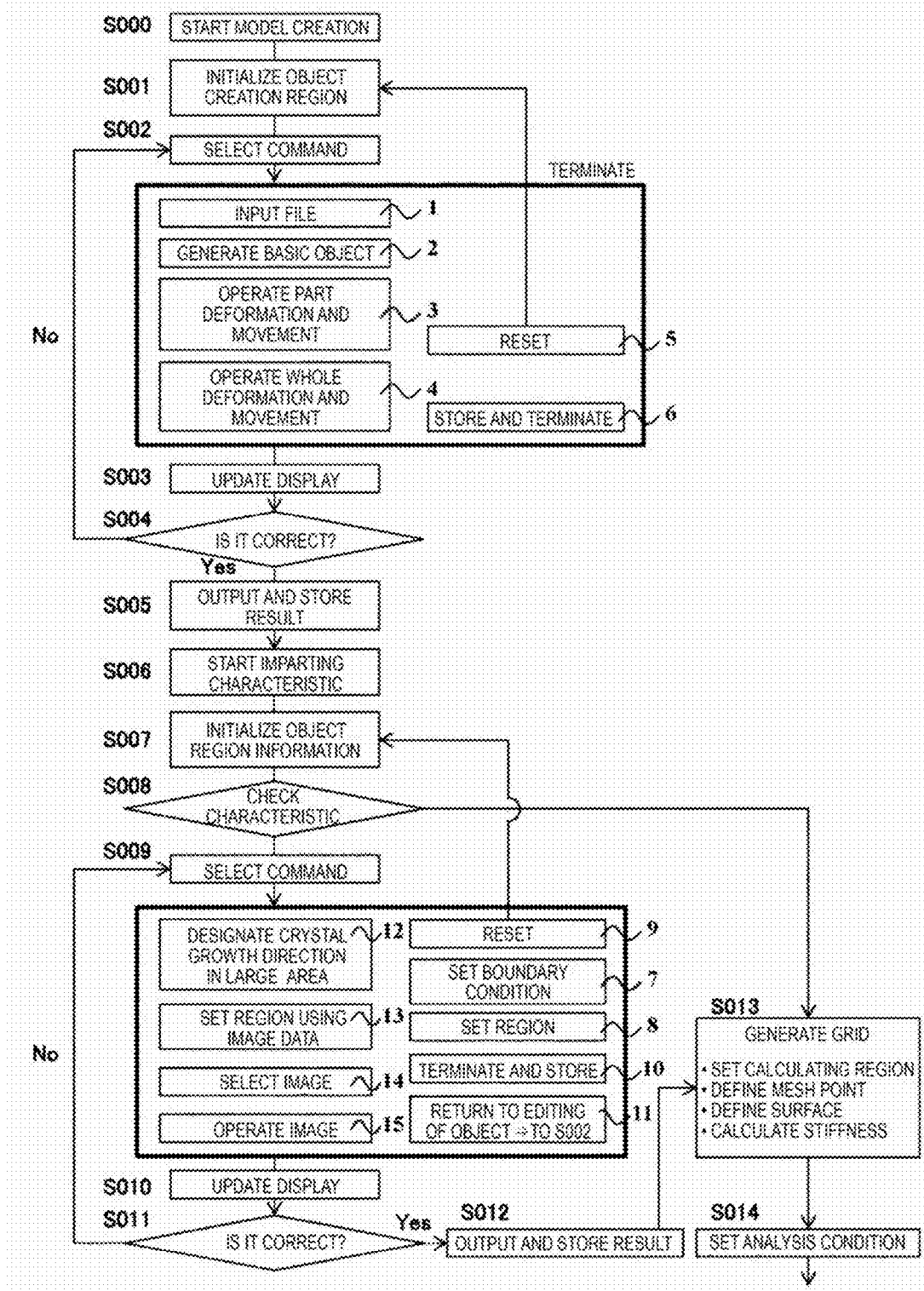

[Fig. 2]
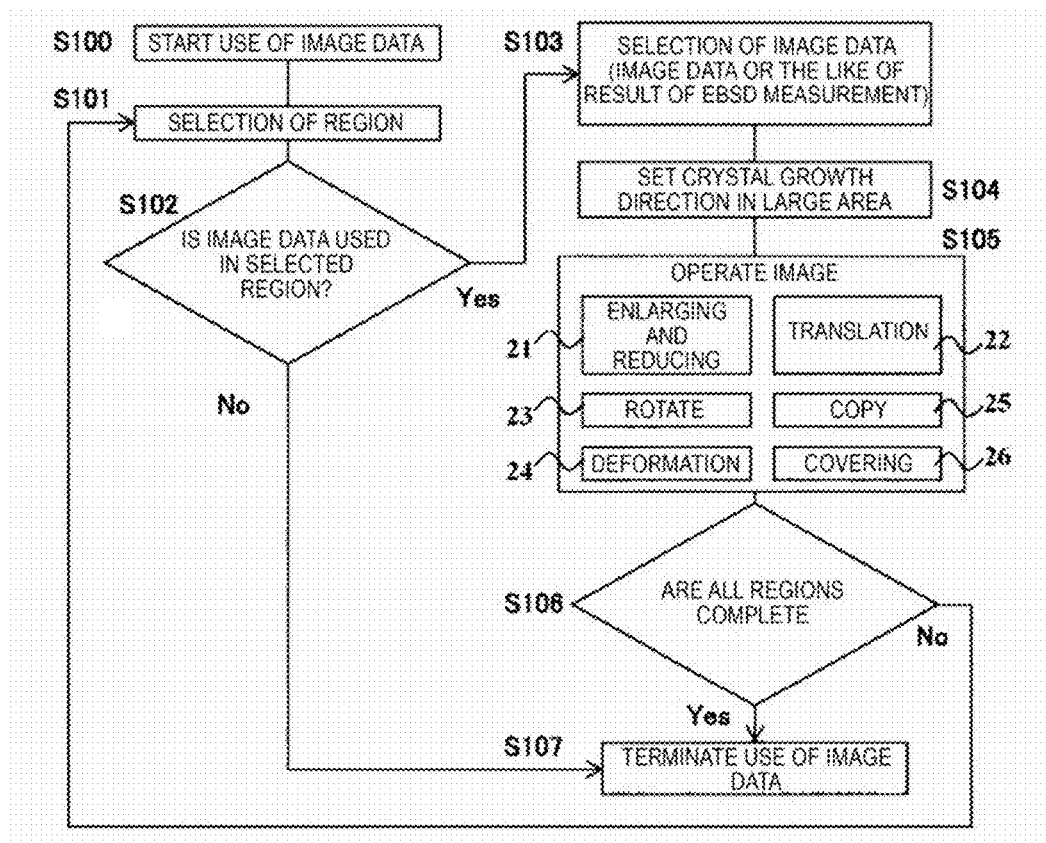

[Fig. 3]
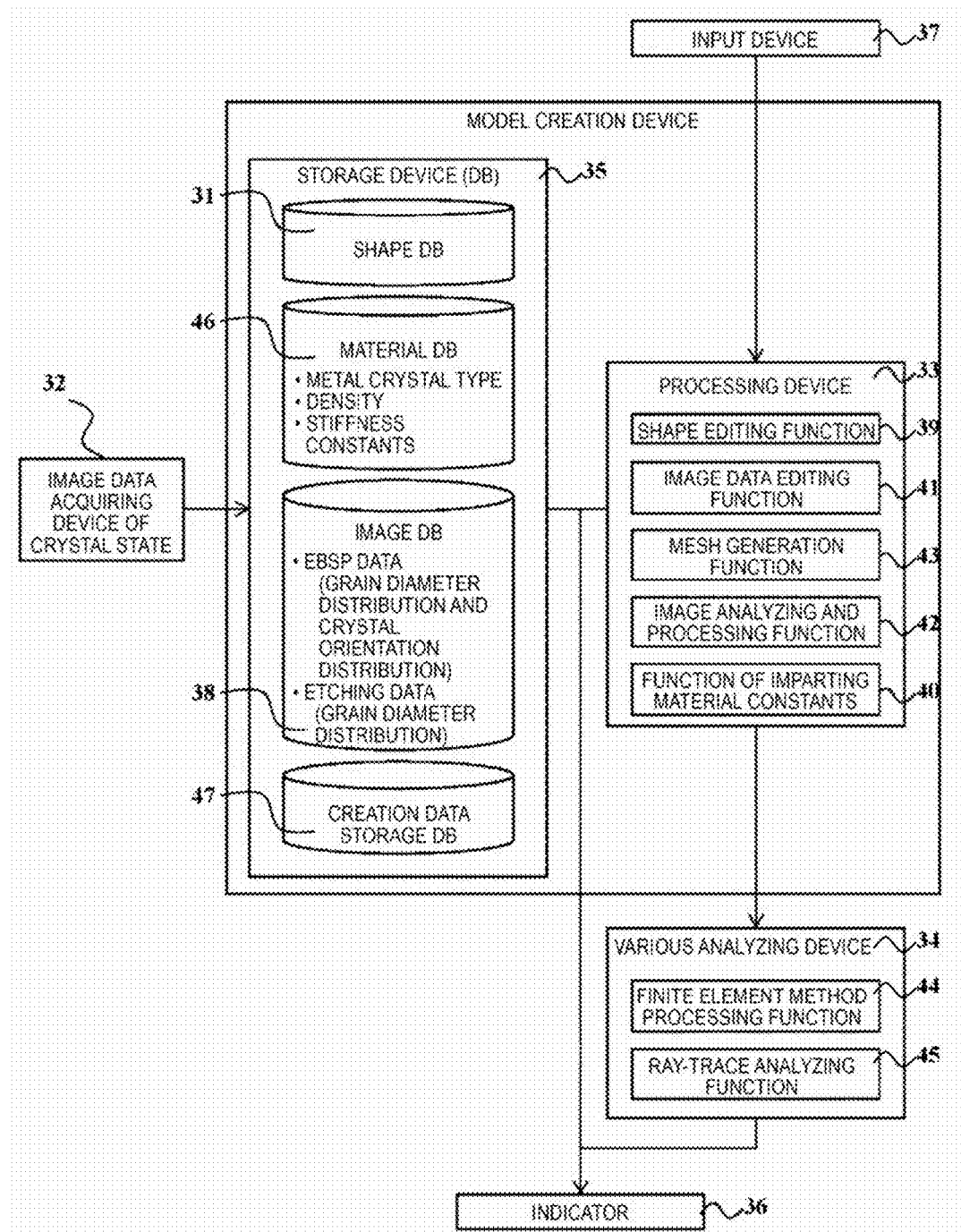

[Fig. 4]
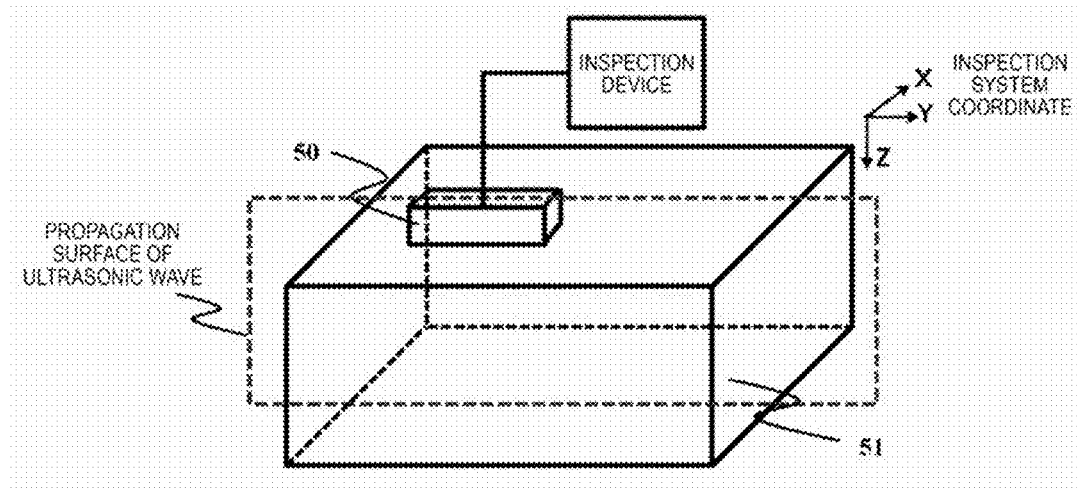

[Fig. 5]
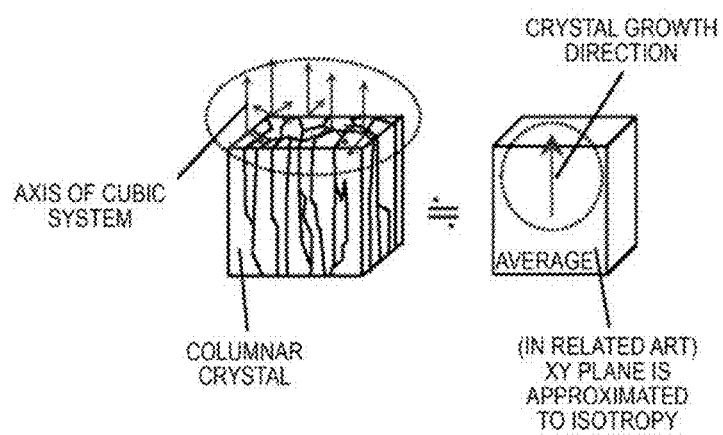
[Fig. 6]
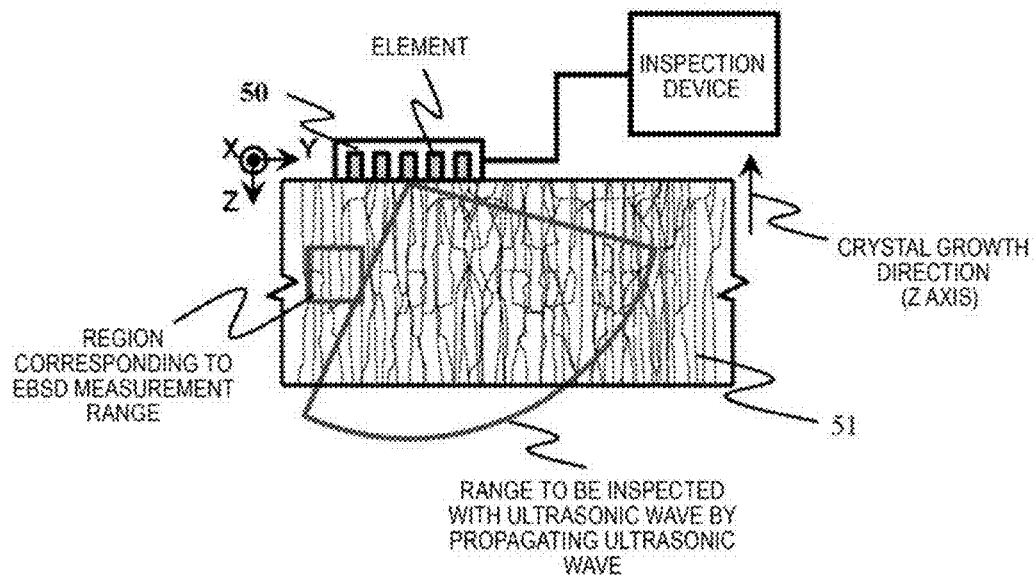

[Fig. 7]
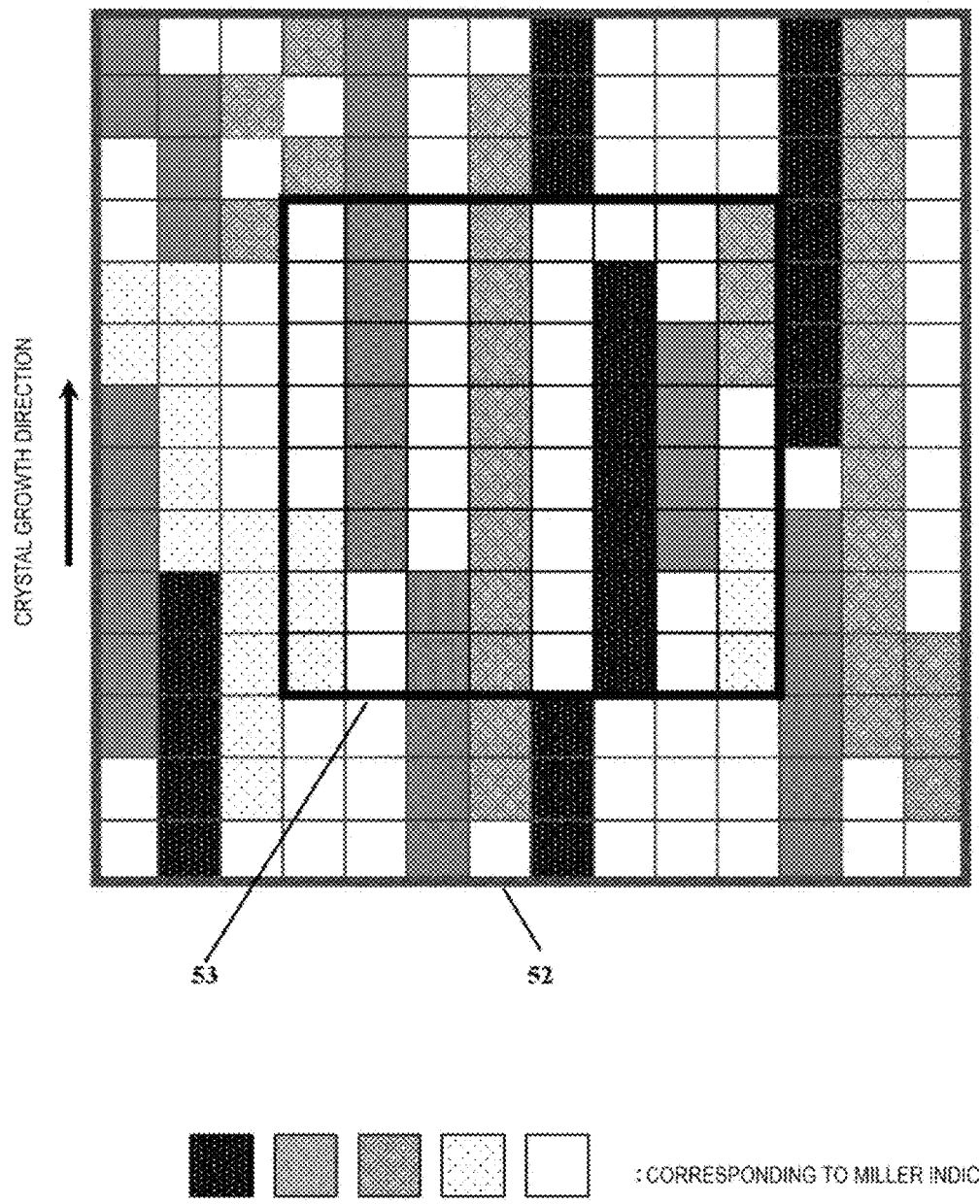

[Fig. 8]
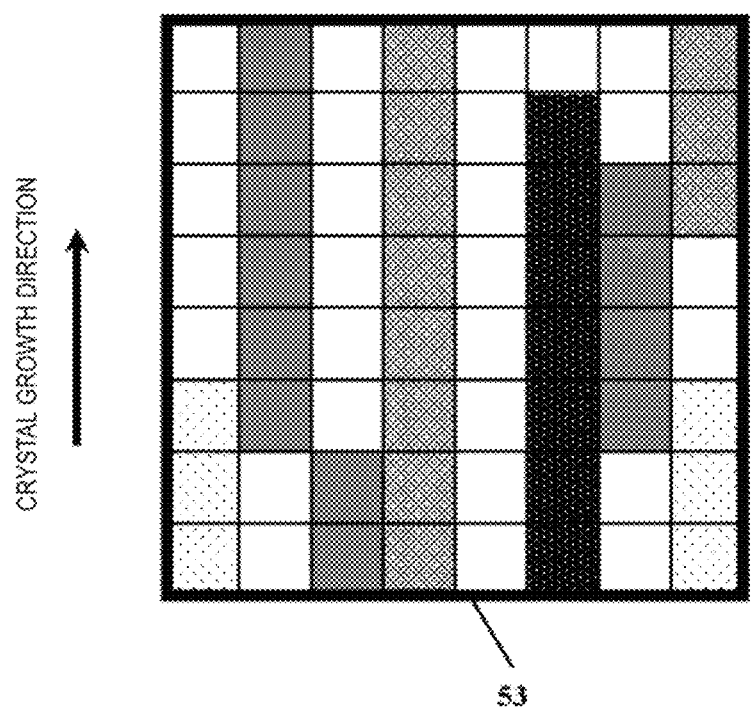

[Fig. 9]
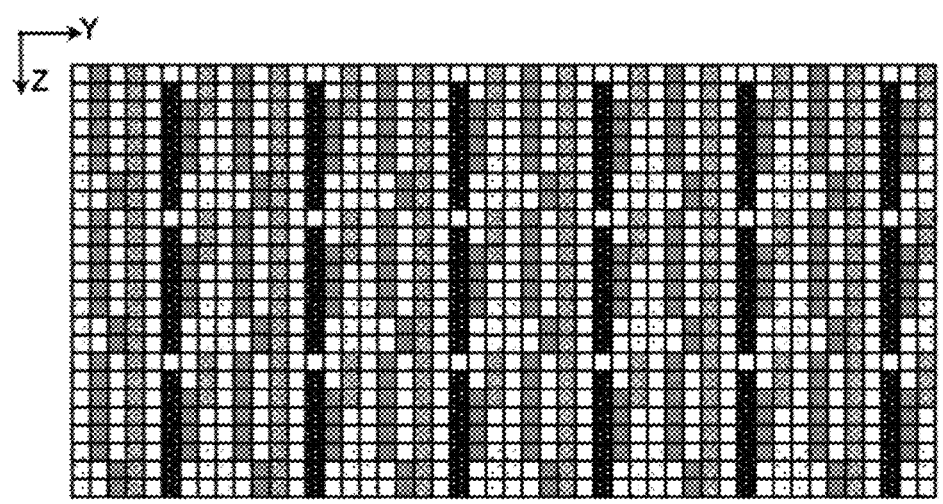
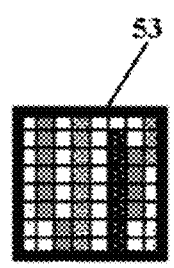

[Fig. 10]
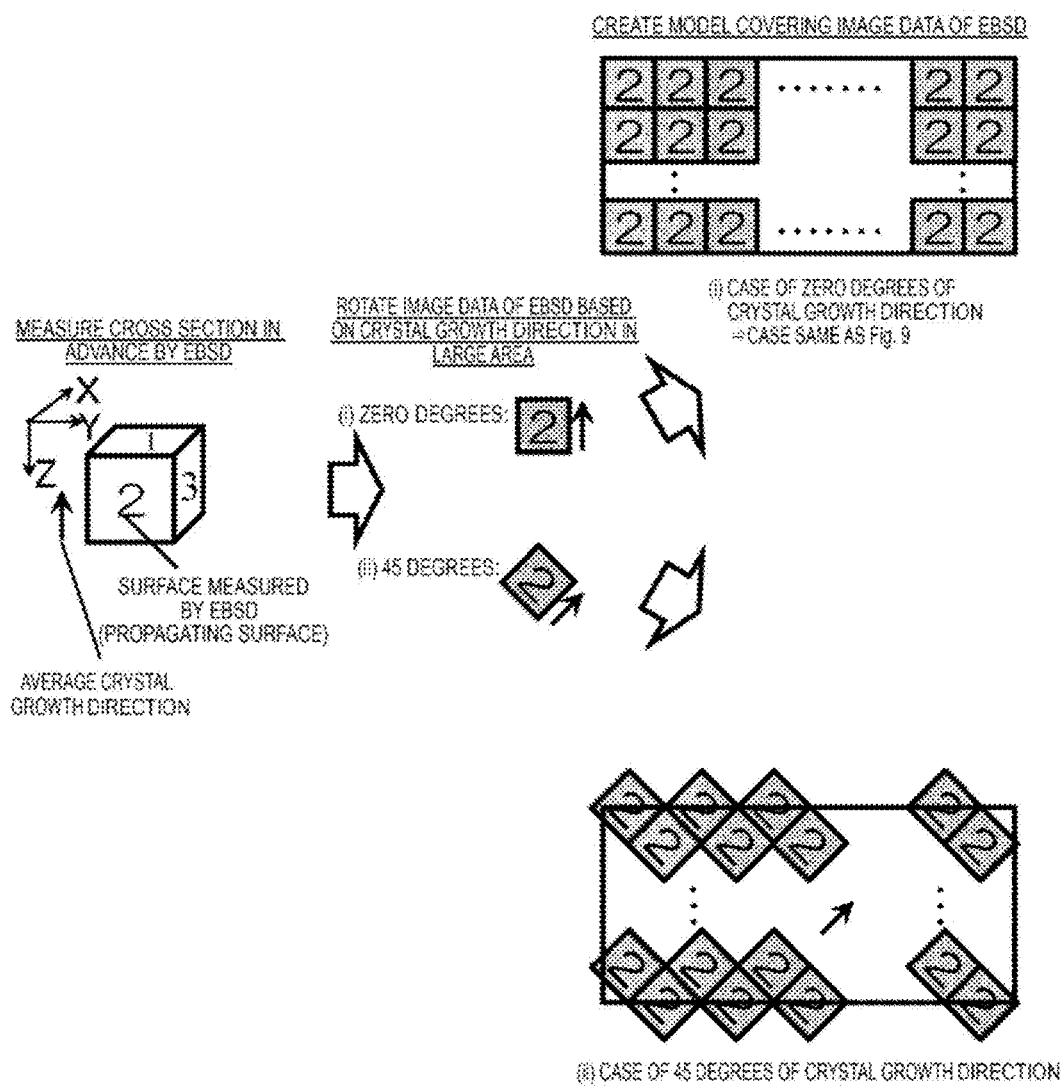

[Fig. 11]
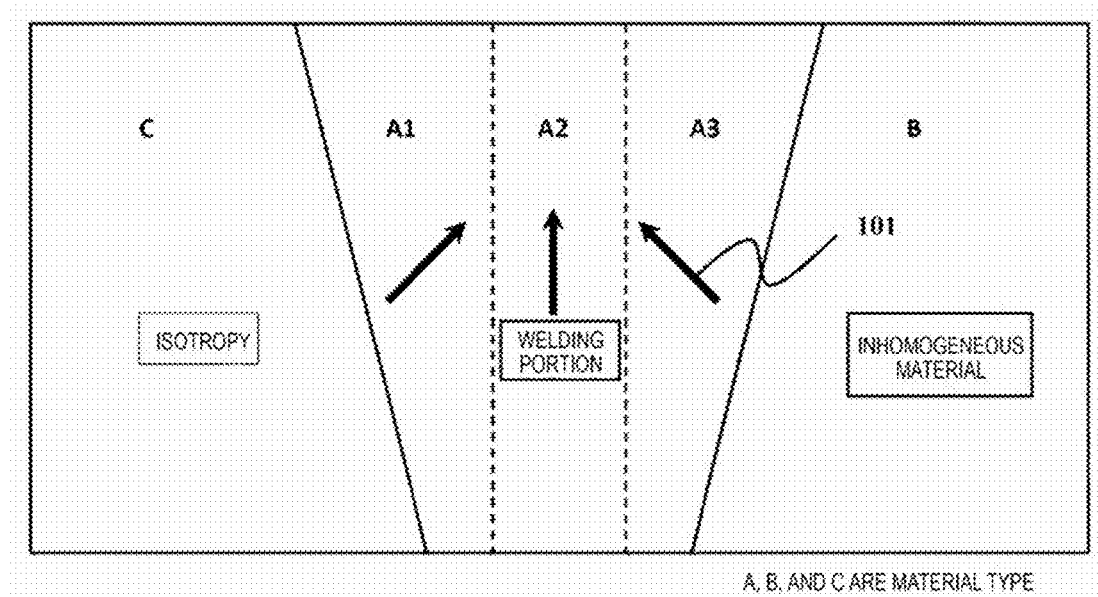
[Fig. 12]
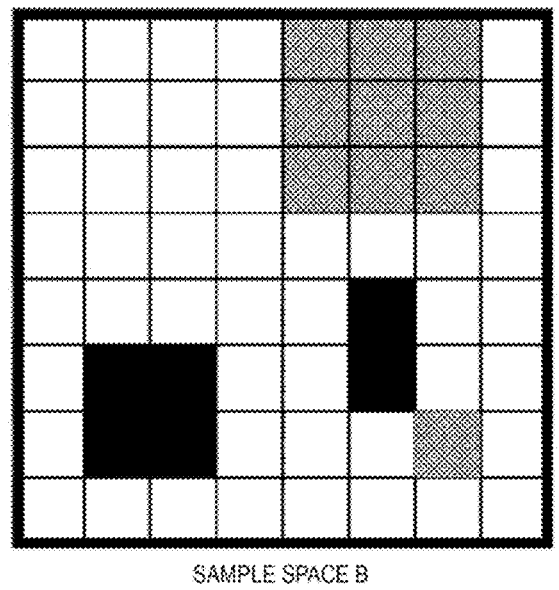

[Fig. 13]
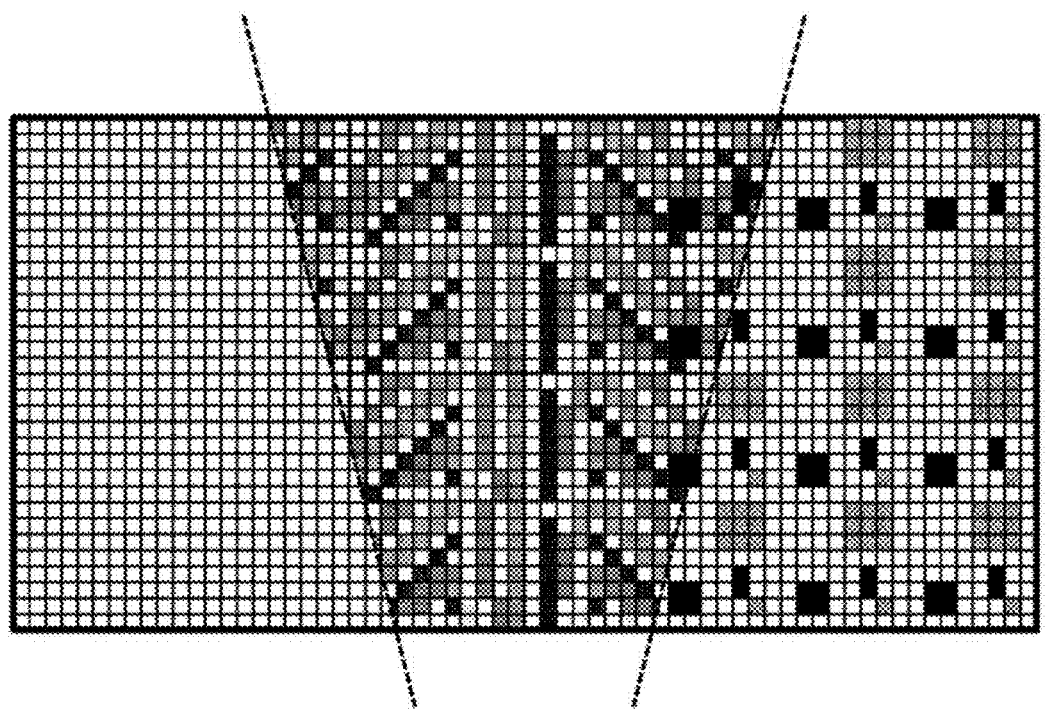

[Fig. 14]
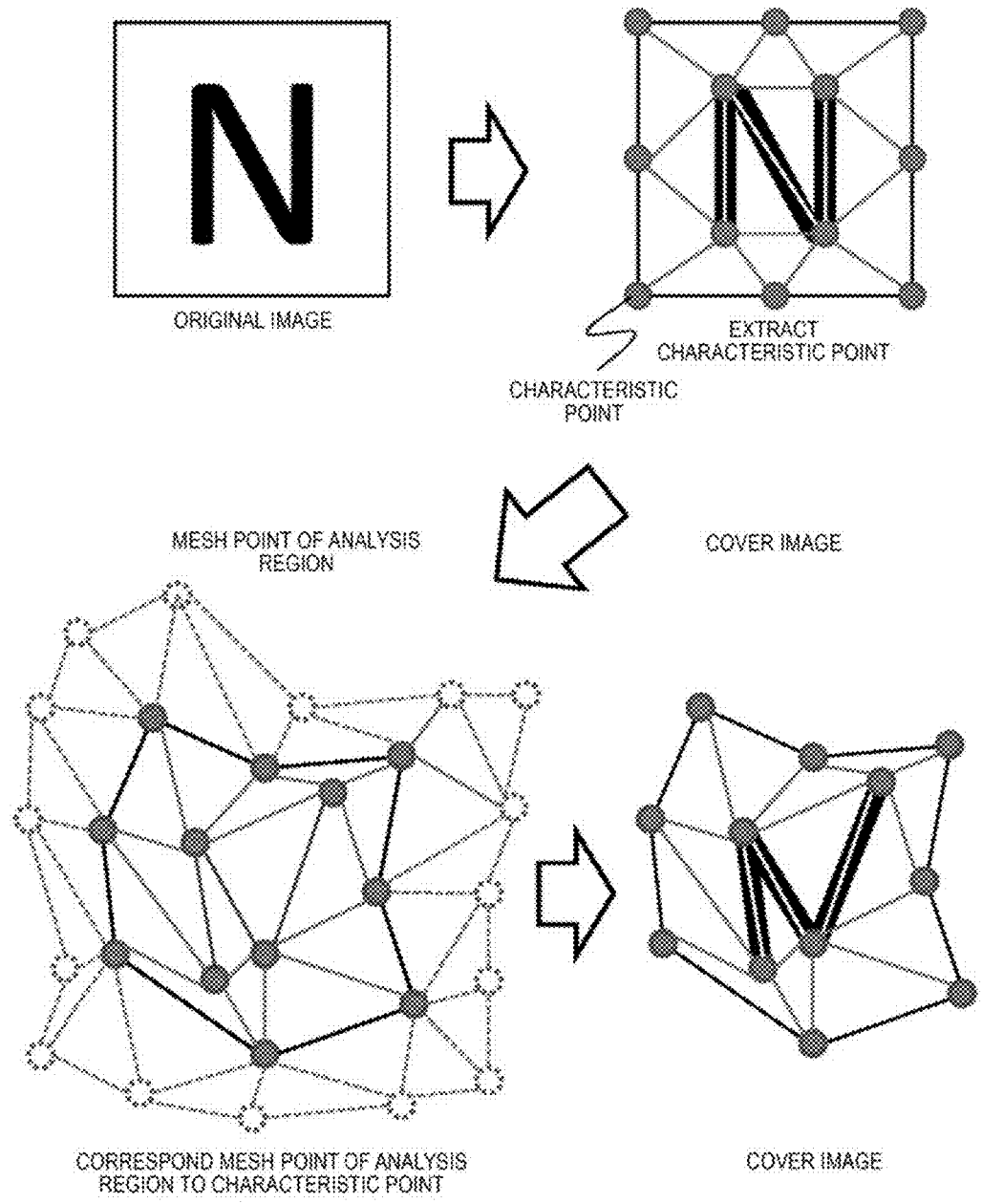

[Fig. 15]
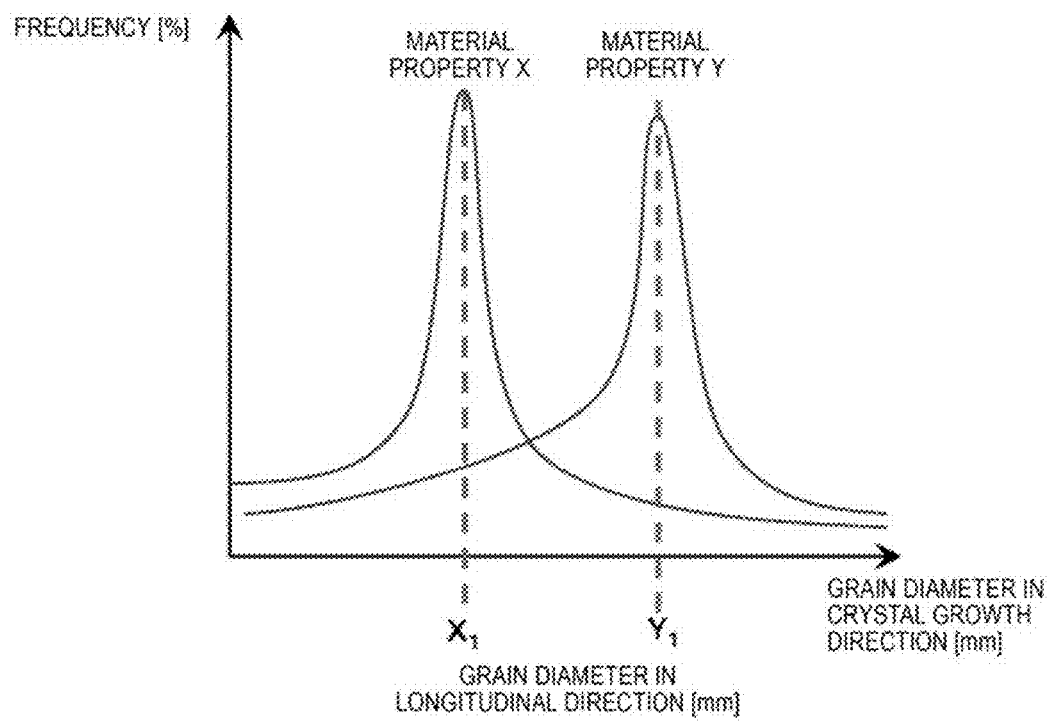
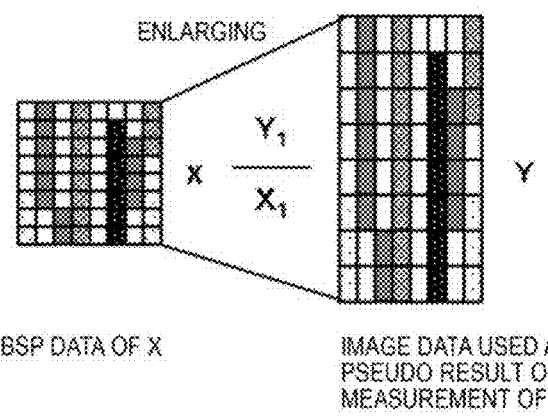

MODEL CREATION METHOD AND DEVICE, AND INSPECTION DEVICE USING THE SAME

TECHNICAL FIELD

The present invention relates to a technology of a propagation analysis of elastic waves, and to a model creation method and device, and an inspection device using the same.

BACKGROUND ART

In inspection or measurement of a structure using ultrasonic waves, in a case in which a material having a coarse crystal grain diameter in which a molten metal is crystallized, or a material having an acoustic anisotropy by growing the crystal grains of the metal along a certain direction is used as a target, it is known that material properties greatly affect a result of the inspection or measurement. The material of the coarse crystal grains is strongly affected by scattering due to a wavelength of an ultrasonic wave, so that an ultrasonic transmission property is deteriorated. Therefore, the wavelength of the ultrasonic wave, which is sufficiently longer than an average grain diameter and is unlikely to be scattered with the crystal grains, is required to be used. In the material having acoustic anisotropy, for example, in a case in which the ultrasonic inspection image is output by isotropic-approximating, a sound velocity depending on a propagation direction cannot be correctly reflected to an inspection image, and thus there is a problem in that position accuracy, or the like is deteriorated. Therefore, it is necessary that the sound velocity depending on a direction where the ultrasonic wave is propagated is calculated and the ultrasonic inspection image is output.

As a member having a great effect on material properties due to such crystallinity being included, a unidirectional solidification material, a metal welding portion, or the like is exemplified. The unidirectional solidification material is made of thin and long crystal grains (columnar crystals), and crystal structures of each of the columnar crystals are the same as each other. Each of the columnar crystals at the time of solidification is aligned toward substantially in a crystal growth direction. However, crystal orientation of each of the columnar crystals in a plane perpendicular to this direction is random. Therefore, if the crystal orientations of all of the columnar crystals are averaged, the material is a material in which the crystal orientation is substantially along only a crystal axis of a longitudinal direction of the crystal grains. In the metal welding portion, the metal is crystallized in a procedure of melting and solidification of the metal, the metal welding portion has a relatively large crystal grain diameter, and there is a tendency that the crystals are grown in a vertical direction when being closer to the center of the welding portion. Therefore, locally, the metal welding portion seems to be a unidirectional solidification material; however, entirely, the metal welding portion is a solidification formation having a different crystal growth direction. Further, a structure including the welding portion is a structure which is divided into a region having the acoustic anisotropy and a region of an acoustic isotropy, when considering that an acoustic isotropic general metal where a sound velocity is not dependent on a propagation direction is bonded. Accordingly, improving of reliability of an output result is important by performing inspection or measurement under consideration of crystal states of the acoustic anisotropy region, or the acoustic isotropy region, and the anisotropy region.

These are known as materials or members which are relatively difficult to inspect or measure using the ultrasonic wave, and elucidation of an ultrasonic propagation phenomenon by numeral analysis is actively carried out. In order to output a simulation result having high reliability, it is important that an accurate model is created under consideration of a crystal state of a structure (distribution of crystal grain or crystal orientation of each crystal grain).

In PTL 1, it is disclosed that the welding portion is divided into a plurality of large regions, and a model including information of a crystal structure and a crystal growth direction is created in every region. A method of generating a model having high accuracy is disclosed, using the created model, and correcting the welding portion model so that a difference between a calculation flaw detection signal, which is an ultrasonic flaw detection signal calculated by a simulation, and the actually measured ultrasonic flaw detection signal is reduced.

CITATION LIST

Patent Literature

PTL 1: JP-A-2012-112658

Non Patent Literature

NPL 1: J. A. Ogilvy, Computerized ultrasonic ray tracing in austenitic steel, NDT INTERNATIONAL. VoL 18. No 2. APRIL 1985

NPL 2: Toshiyuki Koyama, Simulation of Microstructural Evolution Based on the Phase-Field Method and Its Applications to Material Development, J. Japan Inst. Metals, Vol. 73, No. 12 (2009), pp. 891-905

SUMMARY OF INVENTION

Technical Problem

In PTL 1, a region of a welding portion is largely divided, and a model is created using an average crystal growth direction of columnar crystals existing in every divided region. Generally, in a case in which the model is created by focusing on such an average crystal growth direction, even when each micro columnar crystal belongs to a cubic, in macro formation as an aggregate of the columnar crystals, it is a transversely isotropic material of a hexagonal single crystal having the highest rotational symmetry based on the crystal growth direction as an axis. In a case of transversely isotropic material, there are many cases in which the sound velocity of an ultrasonic wave propagating in a subject cannot be accurately reproduced, and for example, a defect position cannot be accurately visualized when inspecting. Therefore, when a propagating phenomenon or a scattering phenomenon of the ultrasonic wave in the welding portion is predicted with high accuracy, or an inspection result is also output with high accuracy based on the predicted data, the crystal state is required to be more precisely modeled than a transversely isotropic material model in the related art.

In addition, if modeling is simply and precisely performed, it can be obtained by an EBSD measurement (Electron Backscattering Diffraction); however, when an accurate analysis model is created by performing the EBSD measurement widely, a test piece is prepared, and is cut into a surface propagating the ultrasonic wave, or a surface executing an ultrasonic propagation simulation, the EBSD measurement, or the like is required to be executed on the cut cross section with time and cost. Therefore, it is difficult to create the accurate analysis model at a low cost and within a short time.

The invention is to provide an accurate analysis model creation method which is capable of simply and quickly creating an analysis model with respect to a structure including a crystalline material.

Solution to Problem

In order to solve the problem described above, according to the invention, there is provided a model creation method of an analysis region used in numeral analysis, the method includes a step of designating a crystal growth direction if a region is a region including crystallinity including acoustic anisotropy in the analysis region, a step of selecting partial image data to which the crystallinity of the region is reflected, a step of rotating and operating the partial image data along the crystal growth direction, and a step of creating image data which is covered in the region designated using the rotated partial image data.

Advantageous Effects of Invention

According to the invention, an accurate analysis model can be simply and quickly created with respect to a structure having the crystalline material.

BRIEF DESCRIPTION OF DRAWINGS

FIG. 1 is a flow diagram illustrating a model creation method.

FIG. 2 is flow diagram illustrating a part to which crystallinity is imparted in a model creation flow.

FIG. 3 is a functional block diagram illustrating the entire configuration of a device.

FIG. 4 is an auxiliary diagram illustrating an inspection system of a unidirectional solidification material.

FIG. 5 is an auxiliary diagram illustrating an approximation model of the unidirectional solidification material.

FIG. 6 is an auxiliary diagram illustrating a cross section at the time of an ultrasonic inspection of the unidirectional solidification material.

FIG. 7 is an auxiliary diagram illustrating an example of a measurement result of the unidirectional solidification material by an EBSD measurement.

FIG. 8 is an auxiliary diagram illustrating a sample space created from an EBSD measurement result.

FIG. 9 is an auxiliary diagram illustrating an example of model creation in a case in which a crystal growth direction corresponds to a Z-axis direction.

FIG. 10 is an auxiliary diagram illustrating a model creation method of the unidirectional solidification material.

FIG. 11 is an auxiliary diagram illustrating a region of a model of a welding portion.

FIG. 12 is an auxiliary diagram illustrating a sample space created from the EBSD measurement result.

FIG. 13 is an auxiliary diagram illustrating an example of model creation of the welding portion.

FIG. 14 is a description view illustrating a coordinate conversion of image data.

FIG. 15 is a description view illustrating a generation method of EBSP data based on grain diameter distribution data.

DESCRIPTION OF EMBODIMENTS

Hereinafter, each of examples of the invention will be described using drawings.

Example 1

In order to provide an accurate analysis model, which is used for simulation techniques to elucidate an ultrasonic propagation phenomenon, inspection image reconstruction techniques by time reversal propagation analysis using an ultrasonic measurement waveform, an ultrasonic inspection condition formulated support, and the like, creation of a model shape and imparting properties to the created model are necessary. A flow to realize the creation of the model shape and imparting characteristics to the created model is illustrated in FIG. 1. S000 to S005 are flows which are necessary at the time of creating the model shape. S006 to S013 are flows for imparting characteristics to the entirety of models using local image data. S014 is a step in which an ultrasonic propagation simulation, an inspection image reconstruction, and an ultrasonic measurement support are assumed using the model created in the invention. Hereinafter, details will be described.

In S000, model creation starts. In S001, initialization of an object (shape) creation region is executed, and in S002, a command selection is executed. In the command selection, there may be a file input command 1 for reading, for example, CAD data, as existing shape data from a shape DB 31, a basic object creation command 2 for generating a basic object, which is for generating a shape, a part deforming and moving operation command 3 for deforming or moving and operating a part of the generated object, a whole deforming and moving operation command 4 for deforming or moving and operating of the whole generated object, or a reset command 5 for resetting the created object, and a storing and terminating command 6 for storing or terminating. After selecting and executing each command, in S003, displaying is updated, and it is determined whether or not the updated object is a desired object in S004. If the determination result is correct, the result is output and stored in S005. If the determination result is not complete or is incorrect, this process returns to the command selection of S002.

Imparting characteristics to the created object starts in S006. In S007, information of the object region is initialized. In S008, as a characteristic check of the created object, it is checked whether or not a member having an acoustic anisotropy (member of crystalline material), a high attenuation material, and the like are included. S008 may be used for activating or deactivating of the command in the command selection in S009. In the command, there may be a boundary condition setting command 7 for creating a boundary having a different material or property and designating boundary characteristics (absorbing boundary, reflective boundary, or the like), which is necessary for generally imparting characteristics, a region setting command 8 for designating basic material data and inputting to a region surrounded by the boundaries, a reset command 9 for resetting information, a terminating and storing command 10 for executing terminating and storing, and a returning command to edit the object 11 capable of editing the object by returning to S002, and the like.

In setting of basic material data with respect to a region surrounded by the boundaries, the basic material data is read out from a storing region or may be able to be input manually using a keyboard, or the like. As the basic material data, in a case of an isotropic material, there may be, for example, material names, density, a longitudinal wave sound velocity, and a transverse wave sound velocity, and in a case of a region having anisotropy, there may be, for example, material names, density, and stiffness constants. If the materials are known-materials, the stiffness constants of the materials may be referred to in a known-database. In a case of polycrystals such as the unidirectional solidification material, it may not always exist in the known-database, in this case, resonance spectrum is calculated using a test piece of the same material in advance by electro-magnetic acoustic resonance (EMAR), and the stiffness constants may be calculated when the resonance spectrum is subjected to the time reversal propagation analysis. Otherwise, the stiffness constants may be calculated theoretically by an ab initio calculation. In addition, there is a crystal growth direction in a large area designation command 12 which is capable of inputting a crystal growth direction in a large area to a position having crystallinity in the region. If the crystal growth direction in a large area is calculated, it may be calculated by preparing a test piece in advance using destructive means, or using non-destructive means. As the destructive means, cross section observation, in which a cross section is observed by cutting a structure, is mainly performed. After polishing and etching the cross section, grain diameter distribution, or the like is found by photographing using optical photographing means. A macro crystal growth direction is found from an X-ray diffraction pattern. As the non-destructive means, a method of theoretically calculating the crystal growth direction based on an equation of Ogilvy (NPL 1), a method of calculating the macro crystal growth direction using a focused ultrasonic measurement (PCT/JP2013/076180), or a method of calculating a solidification phenomenon using a phase-field method simulation (NPL 2) is known, and these methods may be applied to the image data.

Also, in the invention, there are a region using image data setting command 13 for designating a region using image data such as the EBSP data (Electron Backscatter Diffraction Pattern) or image data by etching (photos) from an image DB 38 of a new storing region, an image selection command 14 for selecting an image suitable for a region from various images stored in the image DB 38, an image operation command 15 capable of operating the selected image based on data of the crystal growth direction in a large area, and the like. After selecting and executing each of the commands, in S010, visual information or characteristic information of each region using the image data is updated, and it is determined whether the updated object and the updated characteristic thereof are desired object and characteristic thereof in S011. If the determination result is correct, the result is output and stored in S012, and a grid necessary for a numeral analysis is generated in S013. In a grid generation, a calculation region is set, meshes are generated, and characteristics of defining a mesh point or a surface may be imparted.

As the image data used at the time of imparting stiffness constants, image data generated by an EBSD measurement is appropriately used. Colors of the image data indicated based on a result of the EBSD measurement are correlated with Miller indices, stiffness constants in each mesh may be calculated when a Euler angle is calculated based on the Miller indices indicated using the colors of the corresponding image data and the rotation matrix corresponding to the calculated Euler angle is multiplied by the stiffness constants of the previous basic material data. Moreover, in a case of the unidirectional solidification material, by imparting appropriate crystal surface information to a contrasting density of a photographic image indicating the crystal grain distribution, the result of the EBSD measurement can be pseudo-created. In a case in which the updated object and the updated characteristic thereof are not complete or incorrect in S011, a process returns to the command selection in S009. Of course, in a case in which there is no member having the acoustic anisotropy in S008, this process may progress to generating the grid of S013 and setting of the analysis condition of S014.

Specifically, 10×10×10 mm of a test piece is extracted, and the EBSD measurement is executed at a pitch (for example, 0.01 mm), which is sufficiently smaller than a wavelength of an ultrasonic wave and a size of the crystal grain regarding a surface for propagating the ultrasonic wave. The image data is arranged as illustrated in FIG. 9, and the image data corresponding to an inspection region is created. Also, color information of pixels is read by executing an image process in which the above described pitch is set as one pixel or one mesh (0.01×0.01 mm), and the Miller indices and the Euler angle are calculated from the color or contrasting density of the pixel, so that the Euler angle is reflected to the stiffness constants. Moreover, since the color information based on the image data corresponds to the Miller indices, it is a mechanism of finding the corresponding Euler angle based on the color information. Of course, the color information of the pixel is read by reversely sequentially executing generation of the image data and processing of the pixel, and the stiffness constants corresponding to each pixel are calculated, so that a model in FIG. 9 may be created. FEM, ray trace, or the like is executed to the created model. For example, in a part of model creation in an inspection device using ultrasonic wave (PCT/JP2013/076180), the inspection image reconstruction of the ultrasonic wave can be executed with high accuracy by applying a model creation method of the invention.

In S006 to S014 of imparting parts of the crystallinity in a whole modeling flow of FIG. 1, particularly, a flow using the image data will be described with reference to FIG. 2. In S100, use of the image data starts. In S101, a divided region is selected, and in S102, it is determined whether or not the image data is used for the selected region. In a case in which the image data is used, in S103, the image data substantially matched with a region in the storing region of FIG. 1 is selected. As an optimum image, there is an image in which a crystal grain diameter and the Miller indices of each of the crystal grains are found by the result of the EBSD measurement. In S104, the crystal growth direction in a large area (average) of the selected region is set, and in S105, an operation such as enlarging, reducing, translation, rotation, deformation, copying, or covering of the image is executed with respect to the selected image, and the image data of the selected region is generated. These operations are realized using an enlarging and reducing command 21, a translation command 22, a rotation command 23, a deformation command 24, a copy command 25, and a covering command 26. In S106, it is determined whether or not the whole region using the image data is complete, and in S107, in a case of being complete, a use of the image data is terminated. In S102, even in a case in which the image data is not used, the use of the image data is terminated in S107.

An inspection device including the model creation device by which the above described model generating method can be realized is illustrated in FIG. 3. Basic configuration components of the device are configured as six devices of an image data acquiring device 32 for acquiring image data of a crystal state, a processing device 33 creating a detailed model used for various analyses, a various analyzing device 34 using a created model, a storage device 35 storing various information, an indicator 36 (display) displaying the created data, and an input device 37 inputting various information. The image data acquiring device 32 includes a function of reading the image file acquired by performing, for example, the EBSD measurement on a metal surface, and storing the resultant in the image DB 38 of the storage device. The processing device 33 includes a function of defining an analysis region, which is necessary at the time of the numeral analysis. That is, in order to define the analysis region, the boundary condition is created with a contact medium such as a sensor structure and wedge, a shape and state of an subject, or the like as input information, and a function of dividing the analysis region into meshes is included, and in order to be capable of executing the above described steps, mainly, a shape editing function 39, a function of imparting a material constant to a region 40, an image data editing function 41, an image data analyzing and processing function 42, and a mesh generating function 43 are included.

The shape editing function 39 is a processing unit which executes processes in S000 to S005 in the example. The image data editing function 41 is a processing unit which executes processes in S006 to S014 in the example. The mesh generating function 43 is a processing unit which divides a covered image data by the created image data described above into meshes which are a plurality of pieces, and generates the meshes so as to handle the image data in each small piece unit. The image data analyzing and processing function 42 is a processing unit which reads the color information of the pixel corresponding to each mesh, and calculates the Miller indices and the Euler angle from the color or contrasting density of the pixel. The function of imparting a material constant to a region 40 is a processing unit which calculates the material constant by multiplying the rotation matrix corresponding to the calculated Euler angle by the stiffness constants of the basic material data, imparts the material characteristic to each mesh corresponding to the region using the image data, and creates a subject model used for various analyses. Moreover, when the image data analyzing and processing function 42 reads the color information of the pixel, multiple color information is capable of being included according to a size of the generated meshes. In this case, a process of adopting the color information having the highest proportion in the color information included in the mesh, a process method of substituting with color information of the meshes around the meshes, or the like is considered.

The various analyzing devices 34 include a function which executes a propagating simulation of the ultrasonic wave using the generated model utilizing the image data, for example, a finite element method or a ray-trace analysis method. The various analyzing devices 34 include the finite element method processing function 44 and a ray-trace analyzing function 45. In order to create the analysis region, the storage device 35 includes a shape DB 31 storing a basic shape of the subject, a material DB 46 for storing material data (density, stiffness coefficient, grain diameter distribution, and metal crystal type) constituting the subject, and the image DB 38 storing the image data of the EBSD measurement, optical photographing, or the like. In addition, a created data storage DB 47 storing the created data is also included. The indicator 36 is used for displaying a result obtained by performing analysis by the finite element method, the ray-trace method, or the like, using the created model in order to visualize the edited and created model.

An appropriate ultrasonic inspection system using the model generating method and the device described above is illustrated in FIG. 4. Here, it is assumed that the unidirectional solidification material 51 of a nickel based super alloy is inspected using an ultrasonic array probe 50. A surface surrounded by a dotted line is a propagation surface of the ultrasonic wave. As illustrated in FIG. 5, in a modeling method of the unidirectional solidification material 51 of the nickel based super alloy in the related art, the crystal axis of each of columnar crystals belonging to cubic system is randomly distributed in all directions except for the Z-axis direction, and it is possible to ignore the crystallinity in the X-Y plane in a large area, and thus there are many cases in which the inside of the XY plane is treated as a transversely isotropic approximation in which the sound velocity of the ultrasonic wave is not dependent on propagation directions or as a transversely isotropic material in which crystals are the highest rotational symmetry. In such an approximation, a model to which a crystal axis of each columnar crystal is reflected cannot be created. Here, as the example, the model is created using the image data.

Now, if the crystal growth direction in a large area of the subject in FIG. 4 is assumed to be the Z-axis direction, and the ultrasonic inspection is assumed to be performed using the ultrasonic array probe 50 in a Y-Z plane, as illustrated in FIG. 6, a longitudinal direction of the columnar crystals is arranged substantially along the Z-axis direction in the Y-Z plane to which the ultrasonic wave is applied. In executing modelling using the image data by the EBSD measurement, instead of performing the EBSD measurement on the entire region of the cross section parallel to the Y-Z plane, for example, a unidirectional solidification material sample of the nickel based super alloy corresponding to a range including some degree of the crystal grain or a crystal surface orientation distribution is prepared in advance, and the EBSD measurement is performed on a region corresponding to the propagating surface. A schematic view of a result of the EBSD measurement is illustrated in FIG. 7. Image colors of the result of the EBSD measurement correspond to the Miller indices. In the EBSD measurement region 52, a region where characteristics of the unidirectional solidification material well appear is set to the sample space A 53. The sample space is designated using the input device 37, and the image data designated as illustrated in FIG. 8 may be stored in the image DB 38. If it is found that the crystal growth direction of the unidirectional solidification material is the Z-axis direction in this case, the sample space A 53 is repeatedly moved in parallel and copied along the crystal growth direction in a large area so as to cover the sample space A 53 as illustrated in FIG. 9, and a model of the cross section of the unidirectional solidification material can be created.

A case of the model creation method in which the crystal growth direction of the unidirectional solidification material in FIG. 4 is unknown will be described with reference to FIG. 10. As described above, after calculating the crystal growth direction in a large area, the model may be created by rotating the image data of the result of the EBSD measurement along the crystal growth direction in a large area and covering. At this time, for example, a macro crystal growth direction of the unidirectional solidification material is calculated in a non-destructive manner by the ultrasonic measurement disclosed in (PCT/JP2013/076180), by applying the model creation method of the invention, and modeling the unidirectional solidification material can be executed with high accuracy.

With respect to the created model, a calculating region is set, the meshes are generated, and a characteristic defining a mesh point or surface is imparted. Specifically, with respect to an image by covering the image data which is the result of the EBSD measurement illustrated in FIG. 9, the calculating region is set, and the meshes are generated. In each mesh, the color information is read from the image data, the Euler angle is calculated based on the Miller indices indicated by colors of the corresponding image data, and the rotation matrix corresponding to the calculated Euler angle is multiplied by the stiffness constants of the previous basic material data. Accordingly, the subject model to which the material characteristics of the welding portion used for various analyses are imparted can be created.

According to the example, each general columnar crystal is compared with a model illustrated using an average crystal orientation, and a model, to which the crystal orientation of one by one of each columnar crystal is respectively reflected, can be simply and quickly created with high accuracy.

Example 2

An example of modeling the welding portion will be described with reference to FIG. 11 to FIG. 14. The welding portion is assumed to be configured to have regions A, B, and C as illustrated in FIG. 11. Here, the region A is the welding portion of the previous nickel based super alloy, the region B is an SUS including a highly crystalline impurity, and the region C is SUS in which the material constant is known (isotropic material). A sample space B of the region B is illustrated in FIG. 12, and density and stiffness constants in the sample space can be calculated. A change of the crystal growth direction in a large area in the welding portion can be calculated by using a method disclosed in NPL 1. The change of the crystal growth direction in the region A is approximated to curved lines using a function of the tangent; however, the crystal growth direction in a large area in each region can be approximated to linear shapes by being divided into a plurality of regions.

In the related art, a model is used, which is divided into the regions A1, A2, and A3 as illustrated in FIG. 11, and in which only the crystal growth direction 101 of each region is considered. In the invention, a model illustrated in FIG. 13 can be created using flows illustrated in FIG. 1 and FIG. 2. In the regions A1 to A3, the sample space A is rotated along each of the crystal growth directions, and is covered. In the region B, the sample space B to which a material property including a highly crystalline impurity is reflected is covered. In the region C, the same material constant is imparted because of an isotropic material. In addition, according to a recent image processing technique, since when a pattern is recognized, an image is arbitrarily converted in a distorted space by a general coordinate conversion, or the like so as to be capable of being covered as illustrated in FIG. 14, a method of creating meshes, after making a model by only an image base can be considered.

With respect to such a created model, the calculating region is set, the meshes are generated, and the characteristics defining a mesh point or a surface are imparted. Specifically, with respect to an image in which the image data, which is the result of the EBSD measurement illustrated in FIG. 13, is covered, the calculating region is set, and the meshes are generated. In each mesh, the color information is read from the image data, the Euler angle is calculated based on the Miller indices indicated by colors of the corresponding image data, and the rotation matrix corresponding to the calculated Euler angle is multiplied by the stiffness constants of the previous basic material data. Accordingly, the subject model to which the material characteristics of the welding portion used for various analyses are imparted can be created.

According to the example, a model can be created by a more simple method with respect to a structure configured to have a plurality of members.

Example 3

A sequence creating EBSP data of other materials using one item of the EBSP data will be described using FIG. 15. For example, if there are an unidirectional solidification material X and an unidirectional solidification material Y, the grain diameter distribution of the unidirectional solidification material X and the unidirectional solidification material Y is known. If it is found that only Y of the grain diameter distribution of the crystal growth direction is Y1/X1 times longer than X, and the grain diameter distribution of a direction orthogonal to the crystal growth direction is the same, the image data in which the image data of the result of the EBSD measurement with respect to the unidirectional solidification material X is enlarged Y1/X1 times in the crystal growth direction, is used instead of the result of the EBSD measurement of the Y. At the time of calculating the stiffness constants in each mesh, the data of the Euler angle may be obtained by multiplying the stiffness constants of the Y using the Euler angle in the X by the rotation matrix.

According to the example, it is unnecessary to acquire the EBSP data every time the material is changed, thereby making it possible to create the model by a more simple method.

Moreover, the invention is not limited to the examples described above, and various modification examples are included. For example, the examples described above are described in detail for the sake of easy understanding of the invention, and are not limited to an invention configured to absolutely have all components described. In addition, a part of a configuration of one example can be substituted by a configuration of other examples, and also, a configuration of other examples can be added to a configuration of the one example. Furthermore, additions, omissions, and substitutions of the other configurations can be made to a part of the configuration of each example.

REFERENCE SIGNS LIST

31: shape DB
32: image data acquiring device
33: processing device
34: various analyzing device
35: storage device
36: indicator
37: input device
38: image DB
39: shape editing function
40: function of imparting material constants
41: image data editing function
42: image data analyzing and processing function
43: mesh generation function
44: finite element method processing function
45: ray-trace analyzing function
46: material DB
47: created data storage DB
50: ultrasonic array probe 51: unidirectional solidification material of nickel based super alloy
52: EBSD measurement region
53: sample space A
101: crystal growth direction

The invention claimed is:

1. A model creation method executed by a processing device to create a model of an analysis region used in numerical analysis, the method comprising:
 a step of designating a crystal growth direction for a region including crystallinity having acoustic anisotropy in the analysis region;
 a step of selecting partial image data to which the crystallinity of the region is reflected; and
 a step of rotating and operating the partial image data along the crystal growth direction; and
 a step of creating image data covered in the region designated using the rotated partial image data.

2. The model creation method according to claim 1, wherein the image data is image data of a metal surface acquired by an electron beam backward scattered diffraction device.

3. The model creation method according to claim 1, wherein the image data is image data of a metal surface acquired by optical photographing means after etching the metal surface.

4. The model creation method according to claim 1, wherein the image data is image data generated by a simulation using a phase-field method.

5. The model creation method according to claim 1, further comprising:
 a step of analyzing colors and a contrasting density of a pixel constituting the created image data and calculating a Euler angle;
 a step of calculating a rotation matrix with stiffness constants stored in advance using the calculated Euler angle; and
 a step of imparting the stiffness constants corresponding to the colors or the contrasting density of the pixel to each mesh of an analysis model corresponding to the region using the created image data.

6. The model creation method according to claim 1, wherein, in the step of covering in the region designated using the rotated partial image data, the partial image data in which enlarging or reducing is performed based on grain diameter distribution data is used.

7. The model creation method according to claim 1, wherein the analysis region is constituted by a plurality of regions.

8. A model creation device to create a model of an analysis region used in numerical analysis, the device comprising:
 a storage device that stores a model shape, material data constituting a model, image data indicating crystal orientation of each crystal, and created data; and
 a processing device that executes an image data editing function filling an inside of a region designated using acquired image data, an image data analyzing and processing function which analyzes colors or a contrasting density of the image data and calculates a Euler angle, and a function of imparting material constants which imparts stiffness constants calculated using the Euler angle calculated from the image data to each mesh corresponding to the region designated using the image data.

9. An inspection device comprising:
a finite element method processing function that performs a finite element method from the model created using the model creation device according to claim 8.

10. An inspection device comprising:
a ray-trace analyzing function that performs a ray-trace analysis from the model created using the model creation device according to claim 8.

* * * * *